United States Patent
Archer et al.

(10) Patent No.: US 8,357,534 B2
(45) Date of Patent: Jan. 22, 2013

(54) ISOLATION OF HUMAN ARTICULAR CARTILAGE STEM CELLS

(75) Inventors: Charles William Archer, Aberdare (GB); Samantha Nichola Haven, Cardiff (GB); Gary Dowthwaite, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 215 days.

(21) Appl. No.: 12/526,194

(22) PCT Filed: Feb. 6, 2008

(86) PCT No.: PCT/GB2008/000393
§ 371 (c)(1),
(2), (4) Date: Aug. 6, 2009

(87) PCT Pub. No.: WO2008/096118
PCT Pub. Date: Aug. 14, 2008

(65) Prior Publication Data
US 2010/0098736 A1    Apr. 22, 2010

(30) Foreign Application Priority Data
Feb. 8, 2007  (GB) .................................. 0702401.1

(51) Int. Cl.
*C12N 15/02*    (2006.01)
*C12N 5/00*    (2006.01)

(52) U.S. Cl. .......................... 435/381; 435/373; 435/366
(58) Field of Classification Search .................. None
See application file for complete search history.

(56) References Cited

PUBLICATIONS

Tae et al. Mesenchymal stem cells for tissue engineering and regenerative medicine Biomed. Mater., 2006, vol. 1., pp. 63-71.*
Su, et al., "Cartilage-Derived Stromal Cells: Is It a Novel Cell Resource for Cell Therapy to Regenerate Infarcted Myocardium" Stem Cells, Feb. 2006, vol. 24, No. 2, pp. 349-356.
Alsalameh, et al., "Identification of Mesenchymal Progenitor Cells in Normal and Osteoarthritic Human Articular Cartilage" Arthritis & Rheumatism, vol. 50, No. 5, May 2004, pp. 1522-1532.
"Identification of subpopulations with characteristics of mesenchymal progenitor cells from human osteoarthritic cartilage using triple staining for cell surface markers" Fickert, et al., Arthritis Research & Therapy, 2004, vol. 6, No. 5, pp. R422-R432.
Heng, et al. "Directing Stem Cell Differentiation into the Chondrogenic Lineage in Vitro" Stem Cells; Alphamed Press, Dayton, Ohio, US; vol. 22, No. 7, Jan. 1, 2004, pp. 1152-1167.
Dowthwaite, et al. "The surface of articular cartilage contains a progenitor cell population" Journal of Cell Science, vol. 117, No. 6, Feb. 29, 2004, pp. 889-897.
Rebecca Williams, et al.; "Identification and Clonal Characterisation of a Progenitor Cell Sub-Population in Normal Human Articular Cartilage"; PLoS ONE (www.plosone.org); Oct. 2010, vol. 5, Issue 10, e13246; pp. 1-14.

* cited by examiner

*Primary Examiner* — Deborah Crouch
(74) *Attorney, Agent, or Firm* — King & Schickli, PLLC

(57) ABSTRACT

The invention concerns a human stem cell isolated from the full depth of human cartilage tissue and/or isolated from aged human cartilage; and uses thereof.

5 Claims, 9 Drawing Sheets

Surface

Middle

Deep

Arrows indicate positive intracellular labelling.

ISOLATION OF HUMAN ARTICULAR CARTILAGE STEM CELLS

The invention relates to a novel human stem cell and in particular an articular cartilage stem cell; a population of cells derived therefrom; a method for the production of said stem cell and said population of stem cells; the use of said stem cell and population of cells in tissue repair, and particularly connective tissue repair and more specifically joint repair; and an implant comprising or including said stem cell or said population of cells.

INTRODUCTION

Articular cartilage is avascular, aneural and contains no lymphatic vessels with a low level of metabolic activity compared with that of other connective tissues such as muscle but can be considered active for a cell that relies largely on glycolosis for energy. It also has an extensive extracellular matrix, which it relies upon to provide cartilage with its characteristic properties of low friction pain-free articulation. The two main constituents of articular cartilage are the highly specialised chondrocyte, which is unique to cartilage and the matrix, composed of a complex, interconnecting arrangement of proteoglycans, collagens and non-collagenous proteins (Buckwalter and Hunziker, 1999).

Articular cartilage can be divided into four main zones through its depth. These are the superficial; transitional; upper and lower radial; and calcified cartilage zones running from the outer articular surface to the deep subchondral bone, respectively. Although named zones are present, there are no 'actual' boundaries, which can be visualised between the zones. In each zone there are biomechanical and morphological variations (Dowthwaite et al, 2004), which include differences in cell morphology (size and shape), cell packing, metabolic activity and the thickness of the layers. Differences in matrix composition also exist between zones, with variations in the types and quantities of various collagens, proteoglycans, and non-collagenous proteins.

At most, articular cartilage is only a few millimetres thick, but it can reach up to 7 mm in large joints such as the hip. In spite of being only a few millimetres thick, it still manages to provide resistance to compression and displays the ability to distribute loads, thus in turn, reducing high stresses placed upon subchondral bone (Buckwalter and Hunziker, 1999).

Chondrocytes

Normal articular cartilage contains one cell type, the highly specialised chondrocyte surrounded by extracellular matrix (Buckwalter, 1998). In the majority of cases, the chondrocyte is "cytoplasmically isolated" (Archer and Francis-West, 2003) from its adjacent cells, seldom forming cell-cell contacts except in the most superficial part of the tissue. Each chondrocyte, therefore, is completely surrounded by matrix with which it freely interacts. Chondrocytes differ in their morphology and metabolic activities between the zones of articular cartilage. Generally the chondrocyte has a rounded or polygonal morphology, except at tissue boundaries where it may appear flattened or discoid, i.e. at the articular surface of joints (Archer and Francis-West, 2003). The principal role of the chondrocyte is in the maintenance of the intricate extracellular matrix of cartilage in particular the soluble, hydrophilic structures such as hyaluronan and aggrecan (Knudson, 2003). Intracellularly, the chondrocyte contains organelles that are typical of that of a metabolically active cell (Archer and Francis-West, 2003) that play a pivotal role in matrix synthesis, continually working to synthesise and turn-over a large matrix to volume ratio, primarily composed of proteoglycans, glycosaminoglycans and collagens (Buckwalter and Hunziker, 1999). Some chondrocytes also contain short processes or microvilli, which can detect mechanical alterations in the matrix. This is achieved as they extend from the cell directly into the matrix. Intracytoplastic filaments, lipid, glycogen and secretory vesicles enable chondrocytes to interact with the matrix. Mature chondrocytes are easily distinguished from other cells as they have a spheroidal morphology. They also have abundant amounts of type II collagen, large aggregating proteoglycans and specific non-collagenous proteins interwoven within a meshwork, which forms a cartilaginous matrix that covers and binds to their cell membranes (Buckwalter and Hunziker, 1999).

Zones

Superficial Zone

The superficial zone (FIG. 2) is extremely thin and consists of two layers. The most superficial layer is acellular and consists of a thin, clear film of amorphous material known as the lamina splendens which overlies a sheet of fine, densely packed collagen type II microfibrils (Buckwalter and Hunziker, 1999) and comprises largely lubricin. The deeper cellular layer is composed of flattened, discoid chondrocytes enclosed within a collagen-rich matrix, which lie parallel to the articular surface (Dowthwaite et al, 2003). These cells synthesise matrix, which is abundant in collagen, fibronectin and water, and low in proteoglycans content compared to that of the deeper zones.

The dense layer of collagen fibrils have an orientation parallel to that of the surface and provide cartilage with its characteristic mechanical properties which include having high tensile strength and being able to resist shear force put upon it (Buckwalter and Hunziker, 1999). The meshwork of collagen fibrils also permits the movement of molecules into and out of cartilage such as antibodies and large cartilage molecules respectively.

Various studies have shown that the surface zone of articular cartilage is involved in the regulation of tissue development and growth. Developmental studies in our laboratory have identified that articular cartilage grows by appositional growth from the articular surface (Hayes et al 2001) and that this method of growth allows for the distinct zonal architecture of this heterogeneous tissue to be established. These studies also showed that growth is driven by a slowly dividing population of chondrocytes in the surface zone of articular cartilage and a more rapidly dividing population of cells in the transitional zone (Hayes et al 2001). Not only do these observations account for the appositional nature of articular cartilage growth and zonal variation, they also suggest the presence of a specific articular chondrocyte progenitor cell population in the surface zone and a population of transit amplifying cells in the transitional zone. Further, the surface zone has been found to be a signalling centre due to the expression of various growth factors and their receptors, which play a pivotal role in the morphogenesis of the diarthrodial joint via differential matrix synthesis (Dowthwaite et al, 2003). The surface zone has also been shown in vivo to be responsible for the appositional growth of articular cartilage (Hayes et al, 2001) and recent in vitro studies have shown that the surface zone of articular cartilage contains a progenitor cell population (Dowthwaite et al, 2004).

Additionally, US patent 2006/0239980 teaches that articular cartilage obtained from the surface zone of human cartilage tissue can be enzymatically digested to produce a population of chondrocytes which, through culturing, can be dedifferentiated into chondroprogenitor tissue. However, there is no data in this document concerning the phenotypic stability of this tissue and there is no assertion or indication that the tissue represents isolated stem cells and therefore the use of this dedifferentiated tissue as a reliable source of material for tissue repair is questionable.

In the past we have identified a population of chondroprogenitor cells within the surface zone of bovine articular cartilage (Dowthwaite et al 2004). This population was obtained by exploiting the differential adhesion of bovine chondrocytes to fibronectin. The chondroprogenitors, as well as being characterised by their increased adhesion to fibronectin, also had increased colony-forming efficiency. Further, this chondroprogenitor population exhibited plasticity in terms of its differentiation pathway when assayed in ovo. The bovine chondroprogenitor cells engrafted into various chick connective tissue lineages such as tendon and bone, in addition to cartilage, and the engrafted cells expressed characteristic tissue markers such as type I collagen and, further, orientated in a functional manner.

Recently, we have extended the afore studies and discovered, to our surprise, that it is possible to isolate a population of human stem cells, from the entire depth of human cartilage tissue. This goes against conventional wisdom which teaches that it is the superficial, or surface, zone of cartilage that is responsible for tissue growth and development.

Indeed, our experiments have shown that it is possible to isolate a population of human stem cells from the mid as well as the surface zone of cartilage tissue.

A further surprising aspect to our work is the fact that our stem cells were derived from aged human tissue. Aged human cartilage tends to be thinner than normal cartilage and is metabolically less active.

Moreover, we have discovered that our isolated human stem cells appear immortal in that they have now exceeded 80 population doublings and remain viable. This is in contrast to the above bovine chondroprogenitors that we previously isolated which were characterised by a population doubling of approximately 50 when a number of characteristics of telomerase-dependant senescence was evident. These facts indicate that our bovine chondroprogenitors were not stem cells.

In contrast, our stem cells show self-renewal; as evidenced by the continual population doublings. In order to put our current figure of 80 population doublings into context, one must bear in mind that the Hayflick figure for population doubling is 52. Leonard Hayflick, in 1965, observed that cells dividing in cell culture divide about 50 times before dying. Stem cells which have the ability to continually regenerate new cells survive the entire life span of the endogenous organism.

Furthermore, we have shown that these our human stem cells can still produce cartilage when cultured in permissive pellet culture conditions after 70 population doublings.

It follows that our isolated human stem cells have the capacity to undergo massive expansion with a view to providing new connective tissue and, indeed, the amount of expansion is such that one can replace an entire piece or section of human tissue, such as, cartilage using this single stem cell resource.

Additionally, our novel stem cells exhibit phenotypic plasticity in that these cells can be functionally engrafted into various connective tissue types in order to produce different sorts of connective tissue.

The isolation of our novel tissue involves the exploitation of a unique tissue characteristic. That being the expression of a protein sequence which selectively binds with exceptionally high affinity to an RGD sequence in fibronectin. The RGD sequence in fibronectin comprises the amino acids Arginine, Glycine and Aspartic Acid. A number of cells have the ability to bind to this sequence if cultured for a sufficient length of time (typically hours). In contrast, our stem cells, even after fairly aggressive enzyme isolation, bind the sequence within minutes and, indeed, after 20 minutes, it is possible to isolate a colony comprising our human stem cells.

Finally, the differentiated tissue from this stem cell source expresses at least one structurally relevant protein, namely Type I collagen when engrafted into developing chick connective tissue.

Reference herein to the term stem cell includes reference to a cell that can continuously produce unaltered daughters and also has the ability to produce daughter cells that have different more restricted properties.

Reference herein to a progenitor cell includes reference to a dividing cell with the capacity to differentiate, it includes putative stem cells in which self-renewal has not yet been demonstrated.

As will be apparent to those skilled in the art, cartilage tissue has a limited capacity for self-repair. There are several limitations on the ability of cartilage to repair itself in terms of restoring a long-term functional diarthrodial joint. Chondral repair tissue has an intermediate structure and composition between hyaline cartilage and fibrocartilage, rarely, if ever replicating the actual structure of articular cartilage. There is disruption to the orientation and organisation of the collagen fibrils, failure to make important interactions between macromolecules, in particular the proteoglycans and the collagen fibrillar network, thus resulting in a decrease in stiffness and in the ability to resist compressive loads. A major factor contributing to the low reparative capacities of articular cartilage is that the tissue is avascular and aneural.

Treatments are being developed to try and overcome the problems that are faced when trying to treat articular cartilage defects. Potential treatments need to successfully integrate a tissue into a defect that has the same mechanical and structural properties as articular cartilage. Current cell based transplantation treatments involve the use of expanded autologous chondrocytes for transplantation into the defect to generate a repair tissue hopefully similar to that of the native articular cartilage. This cell based transplantation treatment is known as Autologous Chondrocyte Implantation (ACI) and was described by Brittberg et al (1994) for the treatment of full-thickness cartilage defects. The problem with this technique is that it involves the extraction of healthy articular cartilage from a non-injured, non-weight bearing region of the joint. Contemporary research is looking into the potential use of mesenchymal stem cells (MSCs) as a cell source for use in tissue engineering and their infiltration into biodegradable scaffolds. Bone marrow derived MSCs have been focused on extensively but many other tissue types are now being considered as MSC sources such as cartilage and synovium.

It follows that our stem cells have significant use in cartilage repair. However, our stem cells could be used for the repair of other forms of connective tissue such as ligament, skin or bone.

Further, although our stem cells are suited to autologous repair, particularly cartilage repair, these cells also could be used allogeneically since many other stem cells have been shown to be immunosuppressive.

STATEMENTS OF INVENTION

According to a first aspect of the invention there is provided a human stem cell isolated from aged human cartilage.

Reference herein to aged human cartilage includes reference to cartilage from an adult and most preferably either a mature adult or an adult whose cartilage tends to be thinner than normal cartilage and/or is metabolically less active.

According to a further aspect of the invention there is provided a human stem cell isolated from the full depth of cartilage tissue.

In a preferred embodiment of the invention said human stem cell is isolated from either the surface or mid zone of cartilage tissue or both.

Reference herein to the 'full depth of cartilage tissue' means the whole of the tissue depth from surface to base is used as a source for the stem cell.

According to a yet further aspect of the invention there is provided a human stem cell which is characterised by any one or more of the following traits:
1. its isolation from the full depth of human articular cartilage;
2. its isolation by high affinity adhesion to fibronectin or a fragment thereof containing the RDG sequence;
3. a population doubling in excess of 52;
4. the ability to differentiate into any connective tissue type;
5. the expression of any one or more of the following stem cell markers: STRO1, MSX1 or notch 1;
6. its isolation from human aged cartilage.

According to a further aspect of the invention there is provided a human stem cell population as deposited at the National Institute for Biological Standards and Control (NIBSC) at Blanche Lane, South Mimms, Potters Bar, Hertfordshire EN6 3QG under Accession No. A P-08-016.

According to a yet further aspect of the invention there is provided a population of human connective tissue cells derived from the afore stem cell.

According to a further aspect of the invention there is provided the use of the afore described stem cell in tissue repair.

According to a further aspect of the invention there is provided the use of a population of human connective tissue cells derived from the stem cell described herein in tissue repair.

According to a further aspect of the invention there is provided an implant for use in tissue repair comprising a stem cell, or a population of cells derived therefrom, as described herein.

According to a further aspect of the invention there is provided a method for isolating a human stem cell comprising:
a) obtaining human articular cartilage tissue from the full depth of the cartilage tissue;
b) digesting the tissue to release chondrocytes, by using enzymes;
c) exposing the isolated chondrocytes to fibronectin and/or a fragment thereof containing RGD sequence; and
d) isolating those cells that bind fibronectin or said fragment.

In a preferred method of the invention said released chondrocytes are cultured on fibronectin or a RGD sequence, such as a fragment of fibronectin containing same.

In a further preferred method of the invention said articular cartilage is digested with a combination of pronase and collagenase and more preferably the articular cartilage is exposed to 70 units/ml of pronase for 3 hours at 37° C. followed by exposure to 300 units/ml of collagenase for a longer period, typically overnight, at 37° C.

In yet a further aspect of the invention the digested chondrocytes are either filtered or centrifuged in order to isolate the chondrocytic tissue.

Where centrifugation takes place it is undertaken at 2000 rpm for 5 minutes.

Isolated chondrocytes, preferably, are then seeded into wells coated with fibronectin.

In a preferred method of the invention the articular cartilage tissue is aged tissue.

The invention will now be described with reference to the following figures wherein.

Figure 1:
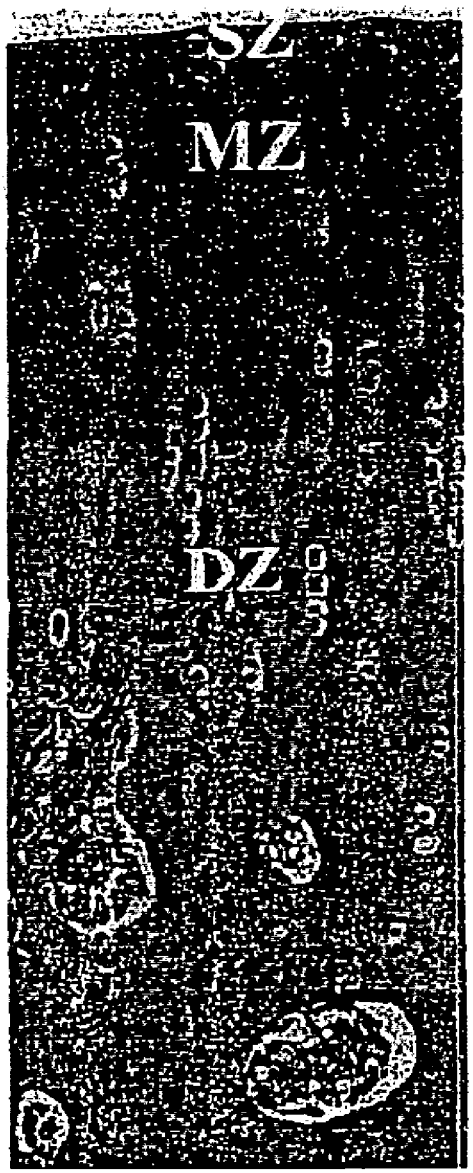
FIG. 1 shows a section through cartilage tissue
Figure 2A:
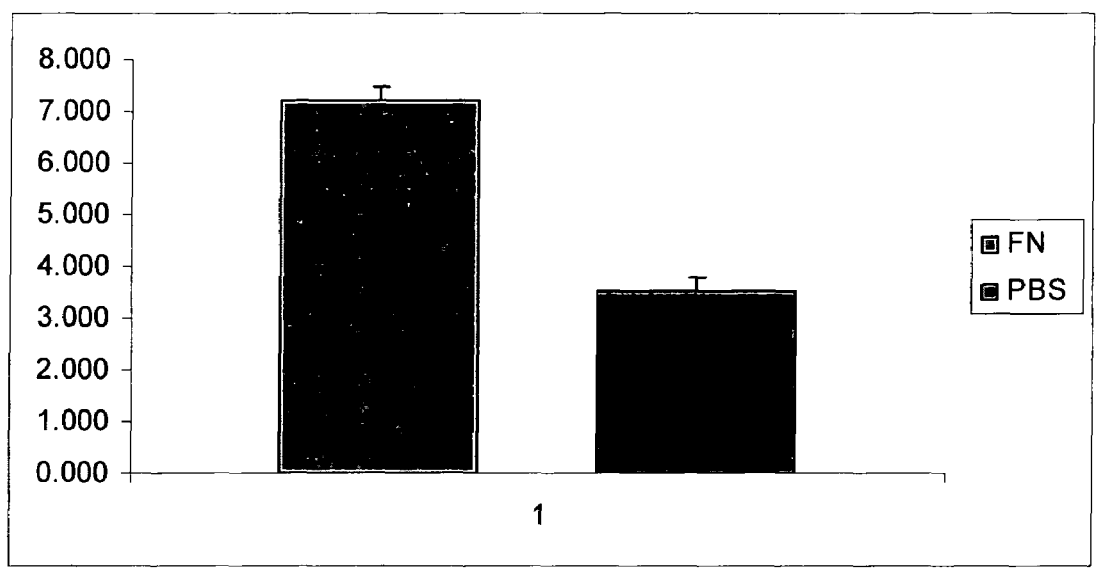
FIG. 2A shows the initial adhesion of human chondrocytes to fibronectin. It was noted that a cohort of chondrocytes adhered to fibronectin within 20 minutes compared to controls ($p<0.05$)
Figure 2B:
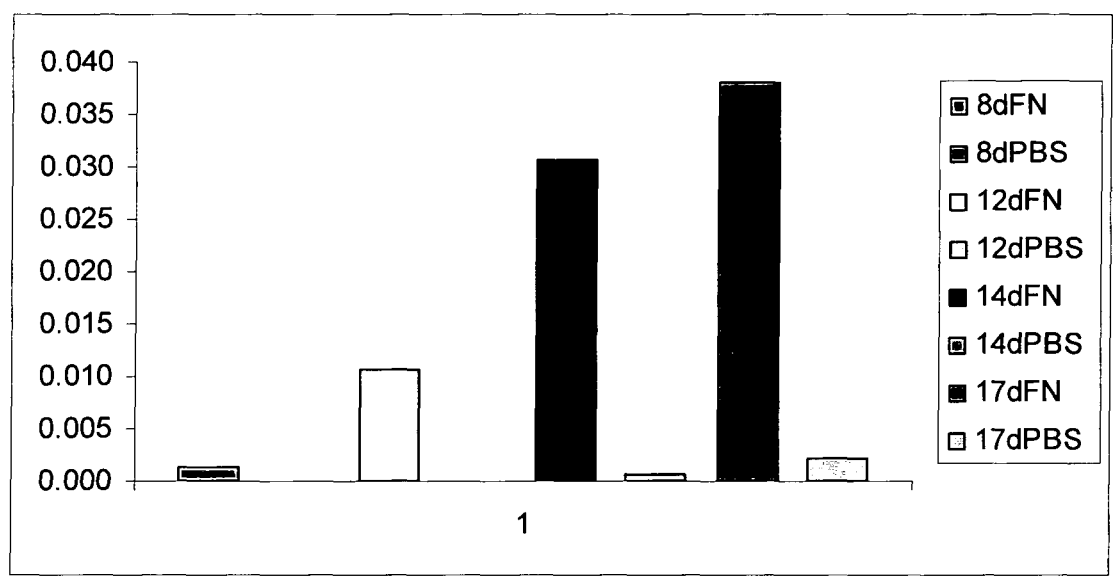
FIG. 2B shows chondrocytes that adhere to fibronectin within 20 minutes can form colonies consisting of more than 32 cells by 8 days and, further the number of colonies increases with time in culture compared with controls ($p<0.05$)
Figure 2C:
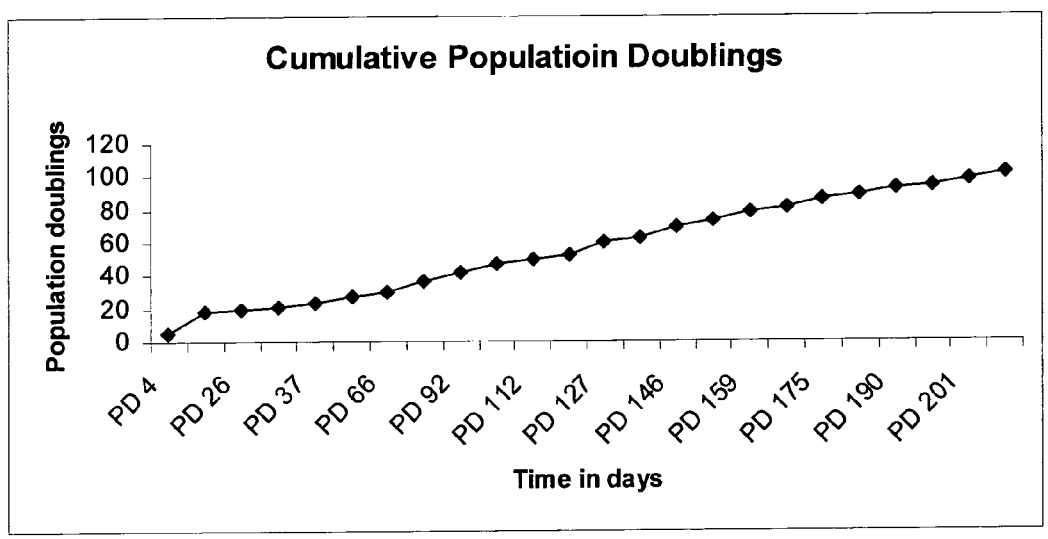
FIG. 2C shows clonally derived human stem cells or chondroprogenitors can be extensively sub-cultured and undergo more than 80 population doublings.
Figure 3A:
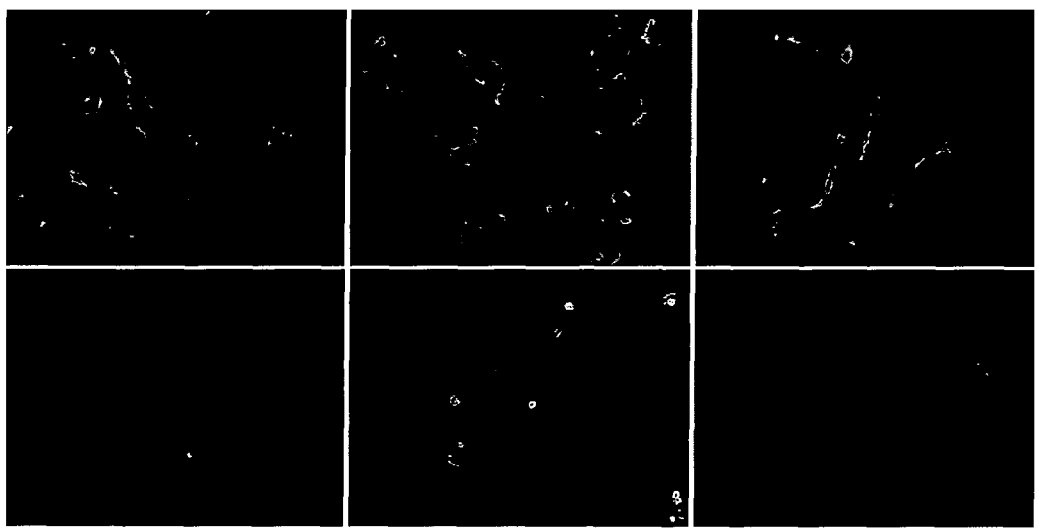
Figure 3B:
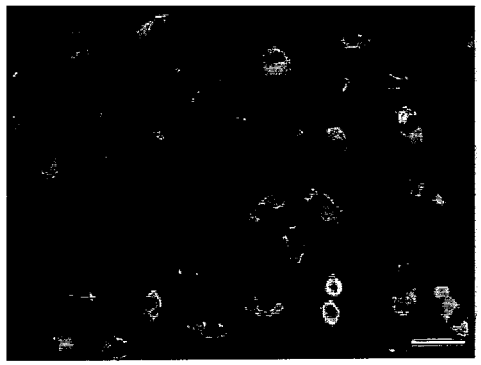
Figure 3B:
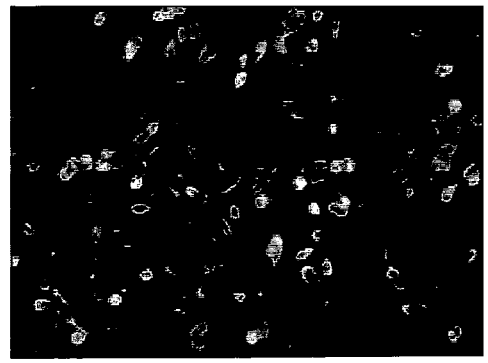
Figure 3C:
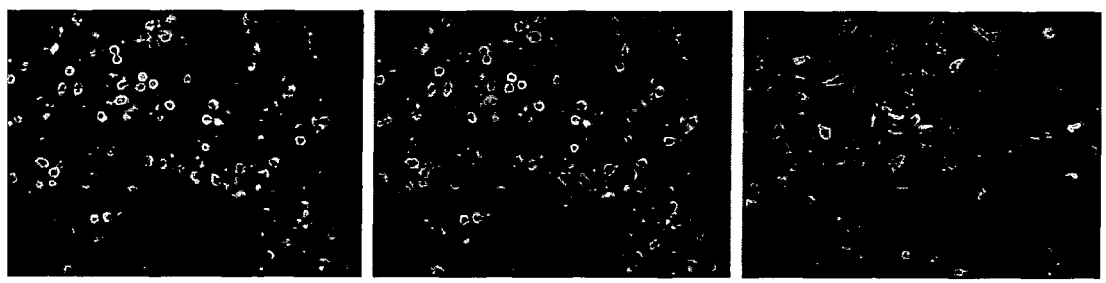
Figure 4:
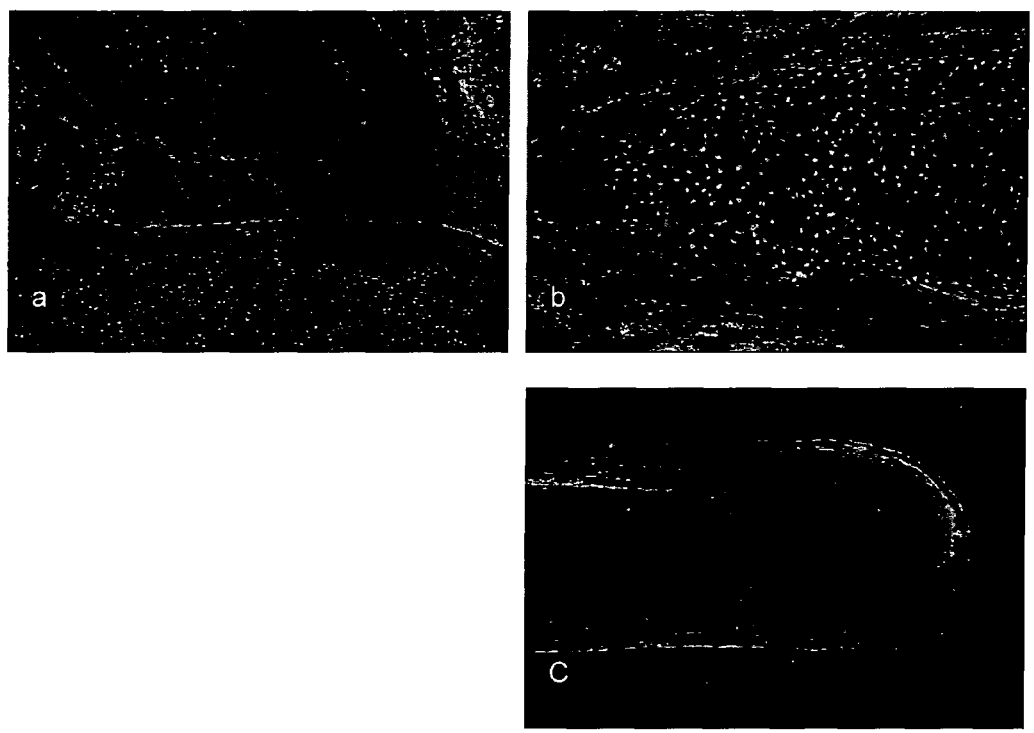
Figure 5:
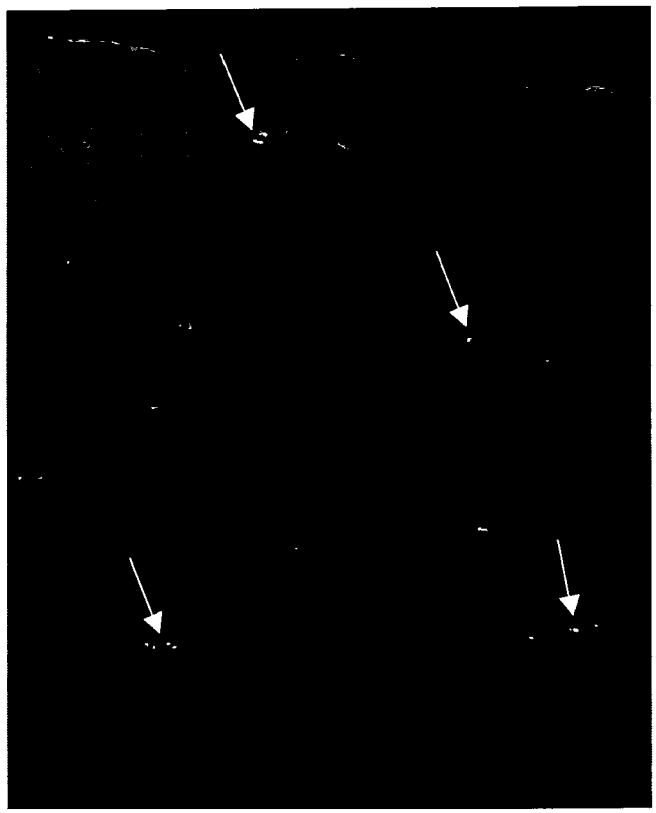

FIG. 3 shows views of clonal cells derived from differential adhesion to fibronectin and unselected cells from the same patient which were immunolabelled with antibodies to the cell surface signalling molecule Notch 1, the stem cell marker STRO1 and the transcription factor MSX1. In clonal cell lines, every cell labelled with antibody to Notch 1 and Stro 1 and the majority of cells labelled with antibody to MSX1. In contrast, monolayer cultures contained fewer cells labelled with antibodies to stem cell markers STRO1, Notch 1 and MSX1 (FIG. 3A-C);

FIG. 4 shows that using an in ovo assay, clonally derived cartilage stem cells were shown to engraft into various chick tissues including, bone, tendon and cartilage and such engrafted stem cells were shown to synthesise a structurally relevant protein, namely human type I collagen (FIG. 4); and FIG. 5 shows wax sections of aged human tissue were labelled with antibody to the transcription factor MSX1 (N20, Santa Cruz Biotechnology; 5 ug ml$^{-1}$ in PBS for 1 hour) and detected with anti-rabbit FITC conjugated secondary antibody (Sigma; 1:100 in PBS for 1 hour). MSX 1 positive cells were present in the surface and middle zones of the tissue suggesting that this is where the stem cells reside within the tissue. Arrows indicate positive intracellular labelling.

MATERIALS AND METHODS 12 well plates were coated with 10 μg ml$^{-1}$ plasma fibronectin (Sigma, UK) in PBS containing 1 mM MgCl$_2$ and 1 mM CaCl$_2$ (PBS+) overnight at 4° C. Dishes were blocked with 1% BSA (Sigma) in PBS+ before chondrocytes were added. Control dishes were treated with PBS+ overnight at 4° C.

Tissue was obtained from patients undergoing hemiarthrotomy with full institutional ethical approval. Full depth cartilage was removed from the grossly normal femoral condyle and incubated in 1:1 DMEM/F12 (Gibco) containing 10% FCS (Gibco) overnight. Chondrocytes were then isolated by sequential pronase (Roche)/collagenase (Sigma) digestion as previously described (Dowthwaite et al 2004). Briefly cartilage chips were incubated with pronase (70 units ml$^{-1}$ in DMEM/F12 containing 5% FCS) for 3 hours at 37° C. Pronase was removed and cartilage incubated with collagenase (300 units ml$^{-1}$ in DMEM/F12 containing 5% FCS) overnight at 37° C. Chondrocytes were centrifuged at 2000 rpm for 5 minutes, supernatant removed and resuspended in serum free DMEM/F12 and counted. After isolation, chondrocytes (1,000 ml$^{-1}$) were seeded into individual wells of 12 well plates and incubated at 37° C. for 20 minutes in 1:1 DMEM/F12 containing 0.1% Gentamycin (DMEM/F12−). After 20 minutes, media (and non-adherent cells) was removed and placed in a second dish for 40 minutes at 37° C. before this media (and non-adherent cells) was removed and placed in a third dish. After removal of media at 20 and 40 minutes, fresh 1:1 DMEM/F12 containing 0.1% Gentamycin and 10% FCS (DMEM/F12+) was added to the remaining adherent cells which were maintained in culture for up to 17 days. Controls comprised cells subjected to differential adhesion on dishes coated with 1% BSA in PBS+.

Within 3 hours of plating, initial chondrocyte adhesion was assayed by counting the total number of cells adhering to the bottom of the dish using an inverted microscope equipped with phase contrast optics and expressed as a percentage of the initial seeding density. Colonies of chondrocytes consisting of more than 32 cells were counted using the same microscope at 8, 12, 14 and 17 days. Colony forming efficiency (CFE) was calculated by dividing the number of colonies by the initial number of adherent cells.

Once colonies consisting of more than 32 cells had formed, they were identified under a light microscope. Clones were trypsinised (0.25%; Gibco) and extensively subcultured in DMEM/F12+10% FCS. Cell numbers were calculated at each passage and population dynamics plotted.

Clonal cell lines were immunolabelled with antibodies to Notch 1 (C20, 5 ug ml$^{-1}$; Santa Cruz Biotechnology), STRO1 (neat TC supernatant, gift from R Oreffo, Southampton University) and MSX1 (N20, 5 ug ml$^{-1}$; Santa Cruz Biotechnology) after fixing for 5 minutes in either 95% EtOH (Notch 1, STRO1) or 10% NBFS (MSX1). Primary antibodies were localised using relevant fluorescently conjugated antibodies and observed under a fluorescent microscope.

Clonal cell lines were labelled with 10 uM cell tracker green (Invitrogen) following the manufacturers instructions and injected into the wing bud of 3 day old (HH St 12-14) chick embryos which had been previously windowed. Embryos were resealed with sellotape and incubated for various times up to day 10 (HH St 36-37) and wings were fixed in 10% NBFS and processed for wax embedding. Samples were sectioned at 10 μm, dewaxed and mounted in DPX before being examined under a fluorescent microscope. Additional sections were immunolabelled with antibody 5D8 (anti human type I collagen; Abcam) and observed under a fluorescence microscope.

As shown in FIG. 5, wax sections of aged human tissue that have been labelled with antibody to the transcription factor MSX 1, a marker for stem cells, showed that stem cells were present in both the surface and middle zones of cartilage tissue. This goes against conventional wisdom which presumed that stem cells were only present in the surface of cartilage tissue.

REFERENCES

Archer C and Francis-West P (2003) The chondrocyte. Int. J Biochem Cell Biol. 35, 401-404.

Brittberg, M, Lindahl, A, Nilsson, A, Ohlsson, C, Isakssin, O, Peterson, L. (1994) Treatment of deep cartilage defects in the knee with autologous chondrocyte transplantation. N Engl J Med. 331, 889-895.

Dowthwaite, G P, Flannery, C R, Lewthwaite, J, Flannelly, J, Archer, C W and Pitsillides A A. (2003) A mechanism underlying the movement requirement for synovial joint cavitation. Matrix Biol. 22, 311-322.

Dowthwaite, G P, Bishop J C, Redman S N, Khan I M, Rooney P, Evans D J, Haughton L, Bayram Z, Boyer S, Thomson B, Wolfe M S, Archer C W. (2004). The surface of articular cartilage contains a progenitor cell population. J Cell Sci. 117, 889-897

Flannery C R, Hughes C E, Schumacher B L, Tudor D, Aydelotte M B, Kuettner K E, Caterson B. (1999) Articular cartilage superficial zone protein (SZP) is homologous to megakaryocyte stimulating factor precursor and Is a multifunctional proteoglycan with potential growth-promoting, cytoprotective, and lubricating properties in cartilage metabolism. Biochem Biophys Res Commun. 254, 535-41.

Hayes, A J, MacPherson, S, Morrison, H, Dowthwaite, G P and Archer, C W (2001). The development of articular cartilage: evidence for an appositional growth mechanism. Anat Embryol. 203, 469-79.

Knudson CB (2003). Hyaluronan and CD44: strategic players for cell-matrix interactions during chondrogenesis and matrix assembly. Birth Defects Res C Embryo Today. 69, 174-96.

The invention claimed is:

1. A method for isolating a human stem cell comprising:
   (a) obtaining human articular cartilage tissue from a full depth of the cartilage tissue;
   (b) digesting the tissue to release chondrocytes, by using enzymes;
   (c) exposing the isolated chondrocytes to fibronectin and/or a fragment thereof containing an RGD sequence; and
   (d) isolating those cells that bind fibronectin or said fragment.

2. A method according to claim 1 wherein said released chondrocytes are cultured on fibronectin, a RGD sequence, or a fragment of fibronectin containing a RGD sequence.

3. A method according to claim 1 wherein said articular cartilage is digested with a combination of pronase and collagenase.

4. A method according to claim 1 wherein said digested chondrocytes are either filtered or centrifuged in order to isolate chondrocyte tissue.

5. A method according to claim 1 wherein the articular cartilage tissue referred to is an aged tissue.

* * * * *